United States Patent
Wang et al.

(10) Patent No.: US 7,875,735 B2
(45) Date of Patent: Jan. 25, 2011

(54) PROCESSES FOR PREPARING ISOFLAVONOIDS USING 7-BENZYLOXY-3-(4-METHOXYPHENYL)-2H-1-BENZOPYRAN AS A STARTING MATERIAL

(75) Inventors: Eng-Chi Wang, Kaohsiung (TW); Sie-Rong Li, Taipei County (TW)

(73) Assignee: KaoHsiung Medical University, Taipei (TW)

( * ) Notice: Subject to any disclaimer, the term of this patent is extended or adjusted under 35 U.S.C. 154(b) by 0 days.

(21) Appl. No.: 12/468,733

(22) Filed: May 19, 2009

(65) Prior Publication Data

US 2010/0298581 A1    Nov. 25, 2010

(51) Int. Cl.
C07D 311/04    (2006.01)
C07D 311/36    (2006.01)

(52) U.S. Cl. ...................... 549/403; 549/406
(58) Field of Classification Search .......... 549/403, 549/406
See application file for complete search history.

(56) References Cited

U.S. PATENT DOCUMENTS

2007/0027329 A1    2/2007    Setchell et al.
2007/0149788 A1    6/2007    Hyatt

FOREIGN PATENT DOCUMENTS

WO    WO 00/49009        8/2000
WO    WO 2005/103025    11/2005

OTHER PUBLICATIONS

Li et al,Tetrahedron Letters, vol. 50, p. 2021-2023 (May 6, 2009).*
Kenneth H. Dudley et al., "Flavonoids. IV. A novel Clemmensen reduction. The direct conversion of 2-alkylisoflavones to 2-alkyl-3-isoflavenes", *J. Org. Chem.*, 1967, 32 (7), pp. 2317-2321.
S. Ramadas et al., "Enantioselective acylation of 2-hydroxymethyl-2,3-dihydrobenzofurans catalysed by lipase from *Pseudomonas cepacia* (Amano PS) and total stereoselective synthesis of (-)-(R)-MEM-protected arthrographol",Tetrahedron: Asymmetry 11 (2000) pp. 3375-3393.
Veselin Maslak et al., "Design, Synthesis, and Conformational Dynamics of a Gated Molecular Basket", J. Am. Chem. Soc. , 2006, 128, pp. 5887-5894.
Rajeev S. Muthyala et al., "Equol, a natural estrogenic metabolite from soy isoflavones: convenient preparation and resolution of R- and S-equols and their differing binding and biological activity through estrogen receptors alpha and beta" Bioorganic & Medicinal Chemistry 12 (2004), pp. 1559-1567.
Santosh J. Gharpure et al., "o-Quinone methide based approach to isoflavans: application to the total syntheses of equol, 3'-hydroxyequol and vestitol" Tetrahedron Letters 49 (2008) pp. 2974-2978.
Jennifer M. Heemstra et al., "Total Synthesis of (S)-Equol" Organic Letters, 2006, vol. 8, No. 24, pp. 5441-5443.
Yu-Chen Chang et al., "Microwave-Mediated Synthesis of Anticarcinogenic Isoflavones from Soybeans" J. Agric. Food Chem., 1994, 42, pp. 1869-1871.
Yuji Takashima et al., "New Synthetic route to (S)-(—)-equol through allylic substitution" Tetrahedron Letters 49 (2008) pp. 5156-5158.
Guan-Yeow Yeap et al., "Synthesis and mesomorphic properties of 7-acyloxy-3-(4-acyloxyphenyl)-4H-1-benzopyran-4-one" Liquid Crystals, vol. 34, No. 5, (2007), pp. 649-654.
Sang-Hun Jung et al., "Structural requirement of isoflavonones for the inhibitory activity of interleukin-5" European Journal of Medicinal Chemistry 38 (2003) pp. 537-545.
Himanshu Singh et al., "A convenient one-pot synthesis of 7-hydroxy-isoflavones from resorcinol with substituted phenylacetic acids", Tetrahendron Letters 47 (2006) pp. 8161-8163.
Francois-Xavier Felpin et al., "Practical and efficient entry to isoflavones by Pd(0)/C-mediated Suzuki-Miyaura reaction. Total synthesis of geranylated isoflavones", Tetrahedron 63 (2007) pp. 3010-3016.
Michael Seeger et al., "Biotransformation of Natural and Synthetic Isofavonoids by Two Recombinant Microbial Enzymes", Applied and Environmental Microbiology, (2003), vol. 69, No. 9, pp. 5045-5050.
Maria Luczkiewicz et al., "Co-cultures of shoots and hairy roots of *Genista tinctoria* L. for synthesis and biotransformation of large amounts of phytoestrogens" Plant Science 169 (2005) pp. 862-871.
M. Miyazawa et al., "Biotransformation of isoflavones by *Aspergillus niger*, as biocatalyst".J. of Molecular Catalysis B: Enzymatic 27 (2004) pp. 91-95.
Paige R. Brooks et al., "Boron Trichloride/Tetra-*n*-Butylammonium Iodide: A Mild, Selective Combination Reagent for the Cleavage of Primary Alkyl Aryl Ethers" J. Org. Chem., vol. 64, No. 26, (1999), pp. 9719-9721.

* cited by examiner

*Primary Examiner*—Bernard Dentz
(74) *Attorney, Agent, or Firm*—Fish & Richardson P.C.

(57)    ABSTRACT

Disclosed herein are processes for the preparation of isoflavonoids, in particular haginin E, equol, daidzein, formononetin and the like, in which 7-benzyloxy-3-(4-methoxyphenyl)-2H-1-benzopyran is used as a common starting material.

14 Claims, No Drawings

PROCESSES FOR PREPARING ISOFLAVONOIDS USING 7-BENZYLOXY-3-(4-METHOXYPHENYL)-2H-1-BENZOPYRAN AS A STARTING MATERIAL

BACKGROUND OF THE INVENTION

1. Field of the Invention

This invention relates to processes for the preparation of isoflavonoids, in particular haginin E, equol, daidzein, formononetin and the like, in which 7-benzyloxy-3-(4-methoxyphenyl)-2H-1-benzopyran is used as a common starting material.

2. Description of the Related Art

Isoflavonoids are one of the six main subclasses of flavonoids and the only one which contains a rearranged $C_{15}$ skeleton based on 3-phenylchroman. The interesting biological properties described for isoflavonoids include antimicrobial, antioxidant, anti-inflammatory, phytoestrogenic and anti-cancer activities. Because isoflavonoids have diverse biological activities, they have attracted the attention of both nature product chemists and synthetic chemists.

Haginin E, equol, daidzein and formononetin are classified into the isoflavonoid family due to their chemical skeletons.

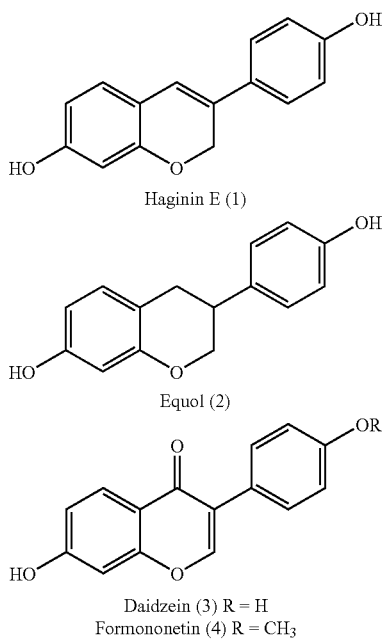

Haginin E (1)

Equol (2)

Daidzein (3) R = H
Formononetin (4) R = CH₃

Haginin E (synonyms: dehydroequol; phenoxodiol; idronoxil; isoflav-3-ene-4',7-diol; 7-hydroxy-3-(4-hydroxyphenyl)-2H-chromene) was first isolated from the stems of *Lespedeza homoloba*, and was initially found to have antioxidative activity against lipid peroxidation in the rat brain homogenate test. More recently, haginin E has been reported to induce apoptosis efficiently in epithelial ovarian carcinoma cells, but having little effect upon normal tissues. In addition, haginin E has been shown to inhibit proliferation in various human cancer cells in vitro and in vivo. Nowadays, haginin E has been subjected to Phase 3 clinical trials for the treatment of ovarian cancer. Nevertheless, the total synthesis of haginin E has received little attention, except for semi-syntheses from daidzein or formononetin.

Equol (synonyms: 4',7-isoflavandiol; 4',7-dihydroxy-isoflavan; 7-hydroxy-3-(4-hydroxyphenyl)-2H-chroman) was first isolated from pregnant mares' urine in 1932 and was subsequently identified in the plasma of sheep (presumably derived from formononetin in red clover) and in human urine (from daidzein)(R. S. Muthyala et al. (2004), *Bioorg. Med. Chem.*, 12:1559-1567). Equol is an isoflavandiol metabolized from daidzein by bacterial flora in the intestines, and it is a chiral molecule that can exist as the enantiomers R-equol and S-equol. Equol is known to have a high binding affinity to estrogen receptors, and causes direct inhibition of the growth of estrogen-dependent breast cancer. In addition, equol has been reported to have potential in anti-prostate cancer and cardiovascular disease therapies due to its bioactivities. Heretofore, only a few synthetic methods for racemic equol have been reported, including the hydrogenation of natural daidzein or formononetin (R. S. Muthyala et al. (2004), supra), and production via a Diels-Alder reaction between o-quinone methides and aryl substituted enol ethers (S. J. Gharpure et al. (2008), *Tetrahedron Lett.*, 49:2974-2978). The racemic equol can be easily separated into (R)- and (S)-forms by chiral HPLC (R. S. Muthyala et at. (2004), supra). Other related chiral synthetic methods, including preparation via intramolecular Buchwald etherification to generate the chroman ring as the key intermediate (J. M. Heemstra et al. (2006), *Org. Lett.*, 8:5441-5443), and synthesis from ethyl L-(−)-lactate via sequential reactions (Y. Takashima and Y. Kobayashi (2008), *Tetrahedron Lett.*, 49:5156-5158), have been directed at (S-equol.

Daidzein (synonyms: 7-hydroxy-3-(4-hydroxyphenyl)-4H-1-benzopyran-4-one; 4',7-dihydroxyisoflavone) and formononetin (synonyms: 7-hydroxy-4'-methoxy-isoflavone; 7-hydroxy-3-(4-methoxyphenyl)chromone; dadein 4'-methyl ether), both of which are found in different amounts in various legumes, such as soy, red clover, etc., have also attracted attention due to their diverse biological activities, such as estrogenic, anti-breast cancer, hormone replacement therapeutic and cancer chemoprevention activities. The methods for isolating daidzein and formononetin from plant materials have distinct drawbacks, including labor-intensive and time-consuming operations, as well as low yields. Most of the synthetic strategies towards daidzein and formononetin include acid-induced cyclization (Y. C. Chang et at (1994), *J. Agric. Food Chem.*, 42:1869-1871; G. Y. Yeap et at. (2007), *Liq. Cryst*, 34:649-654; S. H. Jung et at. (2003), *Eur. J. Med. Chem.*, 38: 537-545; H. Singh and R. Pratap (2006), *Tetrahedron Lett.*, 47:8161-8163), Suzuki-Miyaura cross-coupling (F. X. Felpin et al. (2007), *Tetrahedron*, 63:3010-3016), biotransformation (M. Seeger et al. (2003), *Appl. Environ. Micobio*, 69:5045-5050; M. Luczkiewicz and A. Kokotkiewicz (2005), *Plant Sci.*, 169:862-871; M. Miyazawa et al (2004), *J. Mol. Catal B: Enzym.*, 27:91-95), and other methods.

WO 00/49009 A1 discloses a method for preparing an isoflavan-4-ol of the following formula (II):

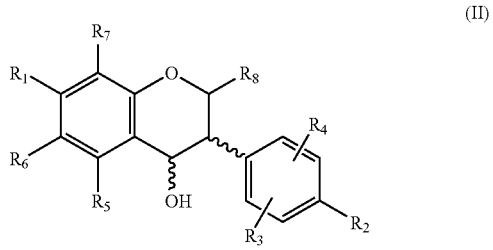

the process comprising hydrogenating an isoflavone of the following formula (I):

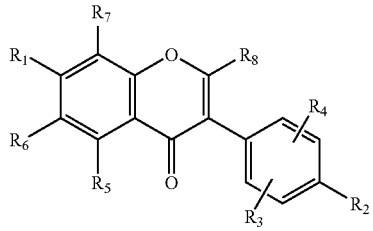

(I)

wherein in formulae (I) and (II), $R_1$, $R_2$, $R_3$, $R_4$, $R_5$, $R_6$, $R_7$ and $R_8$ are independently hydrogen, hydroxy; $OR_9$, $OC(O)R_9$, $OS(O)R_9$, alkyl, haloalkyl, aryl, arylalkyl, thio, alkylthio, amino, alkylamino, dialkylamino, nitro or halo; and $R_9$ is alkyl, haloalkyl, aryl, arylalkyl or alkylaryl.

According to WO 00/49009 A1, the resultant isoflavan-4-ol of formula (II) may be further dehydrated and optionally deprotected or transformed so as to obtain an isoflav-3-ene of the following formula (III):

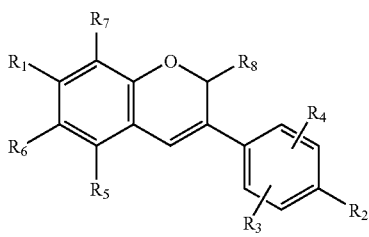

(III)

wherein $R_1$, $R_2$, $R_3$, $R_4$, $R_5$, $R_6$, $R_7$ and $R_8$ are the same as those defined above for formulae (I) and (II).

However, it is noted that the preparation method as disclosed in WO 00/49009 A1 is time-consuming and gives an unsatisfactory yield in the production of haginin E (see Examples 1, 13, 25 and 37 exemplified in the Specification of WO 00/49009 A1).

WO 00/49009 A1 further discloses that the isoflav-3-ene of formula (III) may be hydrogenated to give an isoflavan of the following formula (V):

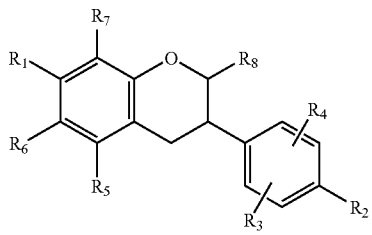

(V)

wherein $R_1$, $R_2$, $R_3$, $R_4$, $R_5$, $R_6$, $R_7$ and $R_8$ are the same as those defined above for formulae (I) and (II).

However, it is noted that the preparation method as disclosed in WO 00/49009 A1 is time-consuming and gives an unsatisfactory yield in the production of equol (see Examples 1, 13, 25, 57 and 59 exemplified in the Specification of WO 00/49009 A1).

WO 2005/103025 A1 discloses a method for preparing a hydroxy-substituted isoflav-3-ene, comprising the steps of hydrogenating a hydroxy-substituted isoflavone in the presence of a basified catalyst to prepare a hydroxy-substituted isoflavan-4-ol, and dehydrating the hydroxy-substituted isoflavan-4-ol. The Examples provided in the Specification of WO 2005/103025 A1 only demonstrate the synthesis of haginin E starting from daidzein. Although it is stated in the Specification of WO 2005/103025 A1 that when the method as disclosed was scaled up, the obtained yield could reach 60-65% and greater, there is no indication of the actual yield as obtained from the Examples exemplified therein.

US 2007/0027329 A1 discloses the synthesis of (S)-equol (see Examples 1-6) and (R)-equol (see Examples 1-4 and 7-8), which starts from daidzein and involves a series of reactions, including end group protection, hydrogenation, reduction, dehydration, enantioselective hydrogenation, and end group deprotection. According to US 2007/0027329 A1, an Ir catalyst having a chiral ligand should be used in the enantioselective hydrogenation. In addition, referring to Example 10 exemplified in the Specification of US 2007/0027329 A1, the intermediate compound as obtained in Example 4 could be deprotected to give haginin E (see Examples 1-4 and 10).

US 2007/0149788 A1 discloses an improved method for preparing (+/−)-equol, comprising reducing an organic diester of daidzein under hydrogen-transfer conditions using palladium hydroxide catalyst.

In spite of the fact that several methods for the synthesis of haginin E, equol, daidzein and formononetin have been reported, some disadvantages still exist, including tedious reaction conditions, low yields and multistep sequences. In addition, the lack of diversity for preparing these compounds is also a shortcoming. Therefore, it is highly desired to develop new preparation processes for these bioactive compounds that are time- and cost-saving while affording a high yield.

Through a thorough analysis of the chemical skeletons of haginin E, equol, daidzein and formononetin, the applicants endeavored to explore a compound that was easy to obtain and could be used as a common starting material for the synthesis of these four bioactive compounds, as well as their analogues. The applicants surprisingly found from retro-synthetic analysis that 7-benzyloxy-3-(4-methoxyphenyl)-2H-1-benzopyran was a perfect candidate for this goal. Based on this finding, the applicants developed new approaches that are simple and efficient in the synthesis of isoflavonoids, in particular haginin E, equol, daidzein, formononetin and the like, while affording a satisfactorily high yield.

SUMMARY OF THE INVENTION

Therefore, according to a first aspect, this invention provides a process for preparing an isoflavonoid, comprising subjecting a compound of formula (I):

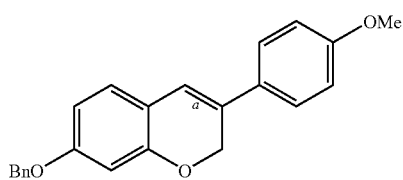

(I)

wherein:

a is a pi-bond;

Bn represents benzyl; and

Me represents methyl;

to at least a chemical reaction so that Bn in formula (I) is released.

In a second aspect, this invention provides a process for preparing equol, comprising subjecting a compound of formula (I) as described above to a first chemical reaction so that in formula (I), a is converted to a single bond and Bn is released, followed by reaction with a demethylating reagent.

In a third aspect, this invention provides a process for preparing a compound of formula (II):

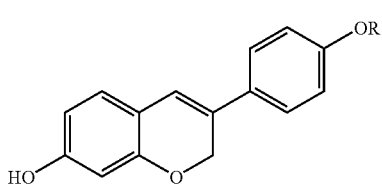

(II)

wherein R represents hydrogen or methyl, the process comprising subjecting a compound of formula (I) as described above to a second chemical reaction using a reagent capable of releasing at least Bn from formula (I).

In a four aspect, this invention provides a process for preparing a compound of formula (III):

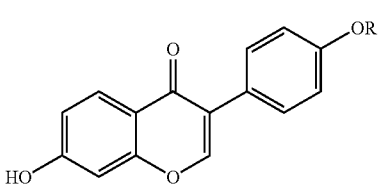

(III)

wherein R is the same as that defined for formula (II) described above, the process comprising:
(i) subjecting a compound of formula (I) as described above to a hydroboration reaction, followed by an oxidation reaction in the presence of a base, so as to form a compound of formula (IV):

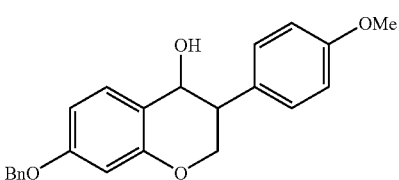

(IV)

wherein Bn and Me are the same as those defined for formula (I) described above;

(ii) converting the compound of formula (IV) to a compound of formula (V):

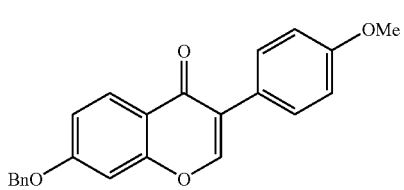

(V)

wherein Bn and Me are the same as those defined for formula (I) described above, by an oxidation-dehydrogenation reaction using 2,3-dichloro-5,6-dicyanobenzoquinone (DDQ); and (iii) subjecting the compound of formula (V) to a third chemical reaction such that at least Bn in formula (V) is released.

The above and other objects, features and advantages of this invention will become apparent with reference to the following detailed description and the preferred embodiments.

DETAILED DESCRIPTION OF THE INVENTION

For the purpose of this specification, it will be clearly understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art, in Taiwan or any other country.

Unless defined otherwise, all technical and scientific terms used herein have the meaning commonly understood by a person skilled in the art to which this invention belongs. One skilled in the art will recognize many methods and materials similar or equivalent to those described herein, which could be used in the practice of the present invention. Indeed, the present invention is in no way limited to the methods and materials described. For clarity, the following definitions are used herein.

In view of the complicated and uneconomical manufacturing procedures for haginin E, equol, daidzein and formononetin, the applicants endeavored to develop new synthetic strategies that were simple and efficient. In particular, the applicants looked for a compound that could act as a common starting material for these four bioactive compounds and the like. Based on a retro-synthetic analysis as shown in the following Scheme 1, the applicants surprisingly found that haginin E, equol, daidzein and formononetin could be derived from an isoflavene 5, i.e., 7-benzyloxy-3-(4-methoxyphenyl)-2H-1-benzopyran, which could be obtained from commercially available resorcinol.

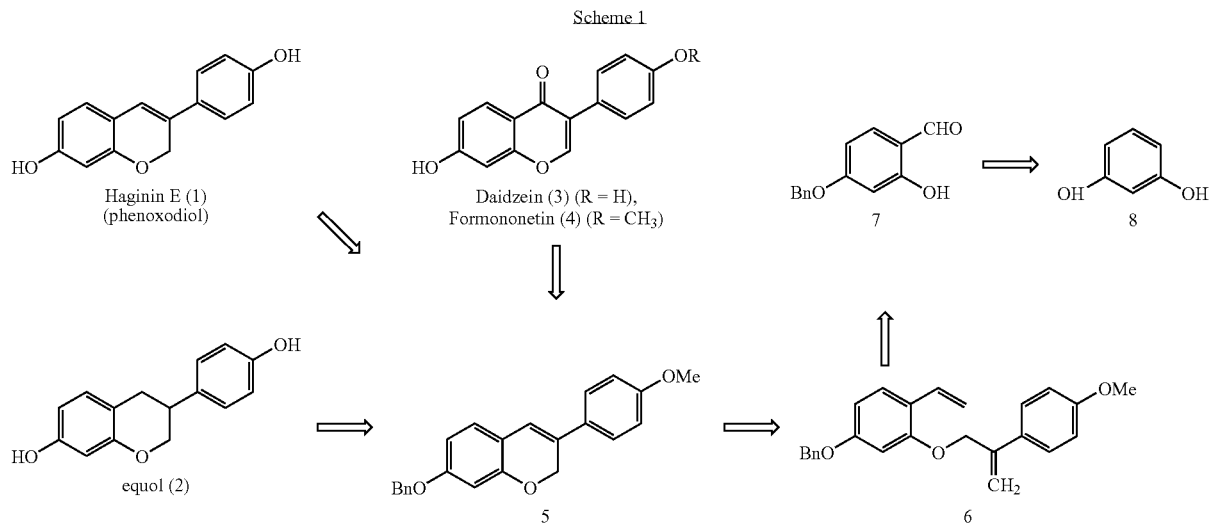

Scheme 1

A new approach that enables the massive production of 7-benzyloxy-3-(4-methoxyphenyl)-2H-1-benzopyran from a novel intermediate compound, i.e., diene 6 shown in the above Scheme 1, is disclosed in the applicants' co-pending application, entitled "Intermediate compounds and processes for the preparation of 7-benzyloxy-3-(4-methoxyphenyl)-2H-1-benzopyran," the whole disclosure of which is incorporated herein by reference.

In this invention, there is provided a process for a process for preparing an isoflavonoid, comprising subjecting a compound of formula (I):

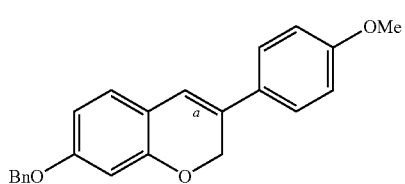

(I)

wherein:
a is a pi-bond;
Bn represents benzyl; and
Me represents methyl;
to at least a chemical reaction so that Bn in formula (I) is released.

The compound of formula (I) can be readily obtained according to the synthetic strategies disclosed in the applicants' co-pending application as described above.

According to this invention, when the isoflavonoid is equol, the process includes subjecting the compound of formula (I) as described above to a first chemical reaction so that in formula (I), a is converted to a single bond and Bn is released, followed by reaction with a demethylating reagent.

According to this invention, the first chemical reaction is conducted in the presence of a suitable catalyst, including, but not being limited to: palladium hydroxide on carbon (Pd (OH)$_2$/C, Pearlman's catalyst), palladium on carbon, etc. In a preferred embodiment of this invention, the first chemical reaction is conducted in the presence of Pd(OH)$_2$/C.

According to this invention, the first chemical reaction is conducted in the presence of a hydrogen donor, including, but not being limited to: cyclohexene, cyclohexadiene, hydrogen gas, ammonium formate, and formic acid. In a preferred embodiment of this invention, the first chemical reaction is conducted in the presence of cyclohexene.

The demethylating reagent suitable for use in this invention includes, but is not limited to: a combination of BCl$_3$ and n-tetrabutylammonium iodide (TBAI, n-Bu$_4$NI); a combination of BCl$_3$ and ethanethiol (EtSH); a combination of AlCl$_3$ and EtSH; a combination of AlCl$_3$ and n-Bu$_4$NI; lithium chloride (LiCl); and sodium ethylthiolate (NaSEt). In a preferred embodiment of this invention, the demethylating reagent is BCl$_3$/n-Bu$_4$NI. In another preferred embodiment of this invention, the demethylating reagent is AlCl$_3$/EtSH.

According to this invention, when the isoflavonoid is a compound of formula (II):

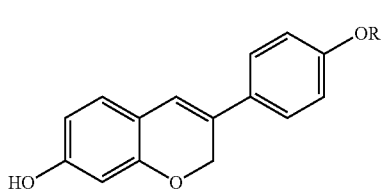

(II)

wherein R represents hydrogen or methyl, the process includes subjecting the compound of formula (I) as described above to a second chemical reaction using a reagent capable of releasing at least Bn from formula (J).

According to this invention, the reagent suitable for use in the second chemical reaction includes, but is not limited to: BCl$_3$; a combination of BCl$_3$ and n-Bu$_4$NI; a combination of BCl$_3$ and EtSH; AlCl$_3$; a combination of AlCl$_3$ and EtSH; a combination of AlCl$_3$ and n-Bu$_4$NI; LiCl; and NaSEt. In a preferred embodiment of this invention, the reagent is BCl$_3$/n-Bu$_4$NI. In another preferred embodiment of this invention, the reagent is BCl$_3$.

According to this invention, when the isoflavonoid is a compound of formula (III),

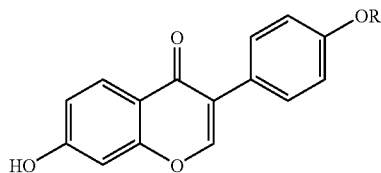

wherein R is the same as that defined for formula (II) described above, the process comprises:
(i) subjecting the compound of formula (I) as described above to a hydroboration reaction, followed by an oxidation reaction in the presence of a base, so as to form a compound of formula (IV):

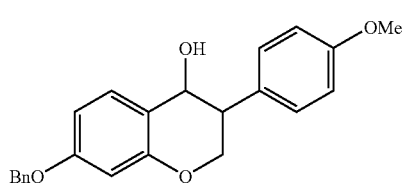

wherein Bn and Me are the same as those defined for formula (I) described above;
(ii) converting the compound of formula (IV) to a compound of formula (V):

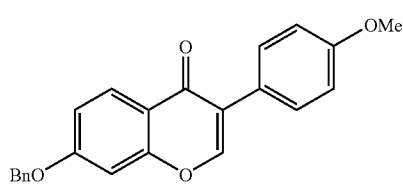

wherein Bn and Me are the same as those defined for formula (I) described above,
by an oxidation-dehydrogenation reaction using 2,3-dichloro-5,6-dicyanobenzoquinone (DDQ); and
(iii) subjecting the compound of formula (V) to a third chemical reaction such that at least Bn in formula (V) is released.

According to this invention, the hydroboration reaction is conducted using a hydroborating reagent, including, but not being limited to: borane-dimethylsulfide complex ($BH_3$—$SMe_2$), $B_2H_6$ and the like. In a preferred embodiment of this invention, the hydroborating reagent is borane-dimethylsulfide complex.

According to this invention, the oxidation reaction is conducted using an oxidizing reagent, including, but not being limited to: $H_2O_2$, $NaBO_3 \cdot 4H_2O$ and the like. In a preferred embodiment of this invention, the oxidizing reagent is $H_2O_2$.

According to this invention, the base suitable for use in the oxidation reaction includes, but is not limited to: NaOH, KOH and the like. In a preferred embodiment of this invention, the base is NaOH.

In a preferred embodiment of this invention, the third chemical reaction is conducted in the presence of a reagent that is capable of releasing at least Bn from formula (V) and is selected from the group consisting of: $BCl_3$; a combination of $BCl_3$ and n-$Bu_4$NI; a combination of $BCl_3$ and EtSH; $AlCl_3$; a combination of $AlCl_3$ and EtSH; a combination of $AlCl_3$ and n-$Bu_4$NI; LiCl; and NaSEt. In a more preferred embodiment of this invention, the third chemical reaction is conducted in the presence of $AlCl_3$/EtSH.

In another preferred embodiment of this invention, the third chemical reaction is conducted in the presence of a catalyst, including, but not being limited to: palladium hydroxide on carbon, palladium on carbon and the like. In a more preferred embodiment of this invention, the third chemical reaction is conducted in the presence of palladium hydroxide on carbon.

According to this invention, when a catalyst is used in the third chemical reaction, a hydrogen donor, including, but not being limited to: cyclohexene, cyclohexadiene, hydrogen gas, ammonium formate, formic acid, will be required.

EXAMPLES

The present invention will be described in more detail with reference to the following examples, which are given for the purpose of illustration only and are not intended to limit the scope of the present invention.

Haginin E, equol, daidzein, formononetin and related compounds can be prepared according to the following reaction scheme and protocols.

As shown in Scheme 2, 7-benzyloxy-3-(4-methoxyphenyl)-2H-1-benzopyran (compound 1) was reacted with n-$Bu_4$NI/$BCl_3$ and $BCl_3$ to give haginin E (compound 2a) at a yield of 79% and 7-hydroxy-3-(4-methoxyphenyl)-2H-1-benzopyran (4'-O-methyl haginin E, compound 2b) at a yield of 81%, respectively. Treatment of compound 1 with Pd(OH)$_2$/C (Pearlman's reagent) and cyclohexene in refluxing ethanol promoted O-debenzylation and reduction of the chromene ring in one step, giving 7-hydroxy-3-(4-methoxyphenyl)-1-benzopyran (compound 3a) at a yield of 94%. Compound 3a was subsequently demethylated by use of n-$Bu_4$NI/$BCl_3$ to give equol (compound 3b) at a yield of 95%.

Using the general procedure of hydroboration-oxidation, compound 1 was converted into a chroman-4-ol (compound 4) at a yield of 60%. Compound 4 was treated with 2,3-dichloro-5,6-dicyanobenzoquinone (DDQ) in refluxing 1,4-dioxane to undergo oxidation-dehydrogenation to give an isoflavone (compound 5) at a yield of 78%. After the deprotection of compound 5 with $AlCl_3$/EtSH, daidzein (compound 6a) was produced at a yield of 92%. On the other hand, compound 5 could be selectively debenzylated with Pearlman's reagent to give formononetin (compound 6b) at a yield of 94%,

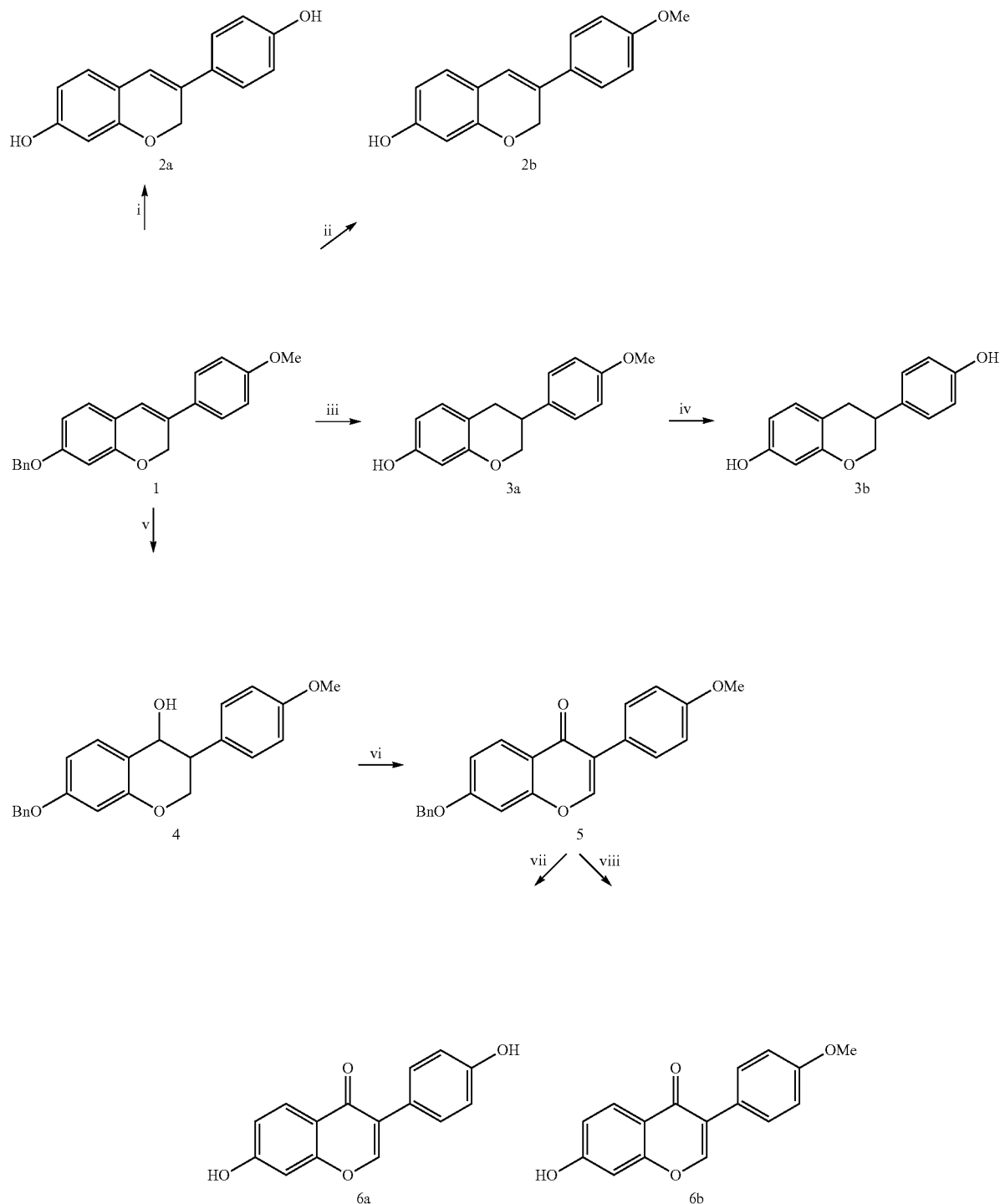
Reagents and reaction conditions:
i. n-Bu₄NI, BCl₃, CH₂Cl₂, -78° C.→ 0° C., 2 hrs;
ii. BCl₃, CH₂Cl₂, 0° C., 10 min;
iii. Pd(OH)₂/C, cyclohexene, ethanol, reflux, 2 hrs;
iv. n-Bu₄NI, BCl₃, CH₂Cl₂, -78° C. → 0° C., 2 hrs;
v. a) BH₃—SMe₂, THF, 0° C., 4 hrs;
   b) 37% H₂O₂, 10% NaOH, 30 min;
vi. DDQ, 1,4-dioxane, reflux, 8 hrs;
vii. AlCl₃, EtSH, CH₂Cl₂, 0° C., 30 min;
viii. Pd(OH)₂/C, cyclohexene, ethanol, reflux, 1 hr.

General Procedures:

The melting point of each of the compounds synthesized in the following examples was detected using an uncorrected Yanaco micro melting-point apparatus.

The column chromatography was performed using silica gel (sieve mesh 230-400 mm, manufactured by E. Merck Company) as the solid phase in combination with a suitable eluent for separation and purification.

$^1$H-NMR and $^{13}$C-NMR spectra were detected using a Varian Gemini-200 or Varian Unity plus 400 spectrometer. Chemical shifts are indicated in parts per million with respect to TMS.

IR spectra were measured on a Perkin Elmer system 2000 FT-IR spectrometer.

Elemental analyses were recorded on a Heraeus CHN—O Rapid analyzer.

Electron impact mass spectra (EI-MS) were recorded on a Chem/hp/middle spectrometer connected to a Hewlett Packard series II model gas-liquid chromatograph.

High-resolution mass spectra (HRMS) were performed on a JEOL JMS SX/SX 102A instrument.

Ex. 1

Synthesis of 7-hydroxy-3-(4-hydroxyphenyl)-2H-1-benzopyran (haginin E, Compound 2a)

The title compound was prepared substantially according to the procedures as described in P. R. Brooks et al (1999), *J. Org. Chem.*, 64:9719-9721, except for minor modifications.

A mixture of 7-benzyloxy-3-(4-methoxyphenyl)-2H-1-benzopyran (1) (0.60 g, 1.74 mmol), n-Bu$_4$NI (2.88 g, 7.83 mmol) and dry CH$_2$Cl$_2$ (15 mL) was stirred and cooled to −78° C. under nitrogen. Thereafter, a solution of BCl$_3$ (1M, 7.83 mL, 7.83 mmol) in CH$_2$Cl$_2$ was added dropwise into the cold mixture. The resultant mixture was stirred and slowly warmed up to 0° C. over 2 hrs. After carefully quenching the reaction with ice water (30 mL), the resultant mixture was stirred for a further 20 min, followed by neutralization with a saturated NaHCO$_3$ solution (30 mL). After concentration in vacuo, the resultant residue was extracted with EtOAc (20 mL×5). The organic layers were combined and dried with anhydrous MgSO$_4$. After filtration, the filtrate was concentrated in vacuo, followed by purification via silica gel column chromatography (ethyl acetate/n-hexane=1;3), thus giving the title compound 2a as a pink crystal (0.33 g, 79% yield).

Detected Properties of the Title Compound:

M.p.: 230-232° C. (lit: 231° C.); R$_f$: 0.19 (ethyl acetate/n-hexane=1:3); IR (KBr) v$_{max}$: 3412, 3034, 1607, 1508, 1437, 1346, 1253, 1152, 826 cm$^{-1}$; $^1$H-NMR (400 MHz, acetone-d$_6$): δ 5.06 (d, J=1.6 Hz, 2H, H-2), 6.32 (d, J=2.4 Hz, 1H, H-8), 6.39 (dd, J=8.4, 2.4 Hz, 1H, H-6), 6.73 (br s, 1H, H-4), 6.85 (d, J=8.8 Hz, 2H, H-3', H-5'), 6.94 (d) J=8.4 Hz, 1H, H-5), 7.34 (d, J=8.8 Hz, 2H, H-2', H-6'), 8.51 (br s, 2H, 2×OH); $^{13}$C-NMR (100 MHz, acetone-d$_6$): δ 68.2, 103.9, 109.9, 116.9, 117.0, 118.8, 127.1, 129.0, 129.3, 129.8, 165.8, 158.5, 159.6; EIMS (70 eV) m/z (relative intensity, %): 241 ([M+1]$^+$, 12), 240 (M$^+$, 75), 239 (100), 165 (12), 147 (10). Anal, calcd for C$_{15}$H$_{12}$O$_3$: C, 74.99; H, 5.03. found: C, 74.61; H, 5.13.

Ex. 2

Synthesis of 7-hydroxy-3-(4-methoxyphenyl)-2H-1-benzopyran (4'-O-methyl haginin E, Compound 2b)

To a stirred solution of compound 1 (0.2 g, 0.58 mmol) in dry CH$_2$Cl$_2$ (4 mL), a solution of BCl$_3$ (1 M, 0.7 mL, 0.7 mmol) in CH$_2$Cl$_2$ was added dropwise at 0° C. under nitrogen. After stirring for 10 min, the mixture was quenched with ice water and a saturated NaHCO$_3$ solution (10 mL), and then stirred for a further 20 min. After extraction with CH$_2$Cl$_2$ (15 mL×6), the organic layers were combined, washed with brine, and dried with anhydrous MgSO$_4$. After filtration, the filtrate was concentrated in vacuo, followed by purification via silica gel column chromatography (ethyl acetate/n-hexane=1:4), thus giving the title compound 2b as a colorless crystal (0.12 g, 81% yield).

Detected Properties of the Tide Compound:

M.p.: 161-163° C. (lit: 158-162° C.); R$_f$: 0.33 (ethyl acetate/n-hexane=1:4); IR (KBr) v$_{max}$: 3452, 2958, 1609, 1514, 1458, 1348, 1276, 1153, 1028, 823 cm$^{-1}$; $^1$H-NMR (400 MHz, CDCl$_3$): δ 3.83 (s, 3H, OCH$_3$), 4.81 (br s, 1H, OH), 5.11 (d, J=1.2 Hz, 2H, H-2), 6.37 (d, J-2.4 Hz, 1H, H-8), 6.39 (dd, J–8.0, 2.4 Hz, 1H, H-6), 6.67 (br s, 1H, H-4), 6.91 (d, J=9.0 Hz, 2H, H-3', H-5'), 6.94 (d, J=8.0 Hz, 1H, H-5), 7.35 (d, J=9.0 Hz, 2H, H-2', H-6'); $^{13}$C-NMR (100 MHz, CDCl$_3$): δ 55.4, 67.3, 103.0, 108.5, 114.2, 116.6, 118.1, 125.8, 127.6, 128.4, 129.5, 154.4, 156.2, 159.3; EIMS (70 eV) m/z (relative intensity, %): 255 ([M+1]$^+$, 15), 254 (M$^+$, 89), 253 (100), 239 (19), 238 (16), 223 (15), 210 (21), 165 (14). Anal. calcd for C$_{16}$H$_{14}$O$_3$: C, 75.57; H, 5.55. found: C, 75.47; H, 5.57.

Ex. 3

Synthesis of 7-hydroxy-3-(4-methoxyphenyl)-1-benzopyran (Compound 3a)

Cyclohexene (1.5 mL) and Pd(OH)$_2$/C (0.15 g) were added to a solution of compound 1 (0.3 g, 0.87 mmol) in ethanol (20 mL). The resultant mixture was stirred under a reflux temperature of 78° C. for 2 hrs, and then cooled to room temperature. After filtration, the filtrate was concentrated in vacuo, followed by purification via silica gel column chromatography (ethyl acetate/n-hexane=1:4), thus giving the title compound 3a as a colorless crystal (0.21 g, 94% yield).

Detected Properties of the Tide Compound:

M.p.: 162-163° C. (lit: 158-160° C.); R$_f$: 0.36 (ethyl acetate/n-hexane=1:4); IR (KBr) v$_{max}$: 3420, 2924, 1609, 1508, 1460, 1336, 1238, 1152, 1115, 1026, 803 cm$^{-1}$; $^1$H-NMR (400 MHz, DMSO-d$_6$): δ 2.82 (m, 2H, H-3 and H-4a), 3.07 (m, 1H, H-4b), 3.73 (s, 3H, OCH$_3$), 3.93 (t, J=10.4 Hz, 1H, H-2a), 4.17 (d, J=10.4 Hz, 1H, H-2b), 6.23 (d, J=2.0 Hz, 1H, H-8), 6.32 (dd, J=8.0, 2.0 Hz, 1H, H-6), 6.87 (d, J=8.0 Hz, 1H, H-6), 6.89 (d, J=8.8 Hz, 2H, H-3', H-5'), 7.22 (d, J=8.8 Hz, 2H, H-2', H-6'), 9.26 (s, 1H, OH); $^{13}$C-NMR (100 MHz, DMSO-d$_6$): δ 31.3, 37.2, 55.1, 70.2, 102.6, 108.2, 112.6, 114.0, 128.5, 130.2, 133.6, 154.6, 156.6, 158.2; EIMS (70 eV) m/z (relative intensity, %): 256 (M$^+$, 30), 135 (18), 134(100), 122(18), 119(14), 91 (13). HRMS calcd for $C_{18}H_{16}O_3Na$ (M$^+$+Na): 279.0997; found: 279.0999.

Ex. 4

Synthesis of 7-hydroxy-3-(4-hydroxyphenyl)-1-benzopyran (equol, Compound 3b)

The title compound was prepared substantially according to the procedures as described in P. R. Brooks et al. (1999), supra, except for minor modifications.

A mixture of compound 3a (0.20 g, 0.78 mmol) as obtained in the above Example 3, n-Bu$_4$NI (1.01 g, 2.73 mmol) and dry $CH_2Cl_2$ (5 mL) was stirred and cooled to −78° C. under nitrogen. Thereafter, a solution of BCl$_3$ (1M, 2.73 mL, 2.73 mmol) in $CH_2Cl_2$ was added dropwise into the cold mixture. The resultant mixture was stirred and slowly warmed up to 0° C. over 2 hrs. After carefully quenching with ice water (10 mL), the mixture was stirred for a further 20 min, followed by neutralization with a saturated NaHCO$_3$ solution (10 mL). After concentration in vacuo, the resultant residue was extracted with EtOAc (10 mL×5). The organic layers were combined and dried with anhydrous MgSO$_4$. After filtration, the filtrate was concentrated in vacuo, followed by purification via silica gel column chromatography (ethyl acetate/n-hexane=1:3), thus giving the title compound 3b as a colorless crystal (0.18 g, 95% yield).

Detected Properties of the Title Compound:

M.p.: 162-164° C. (lit: 158° C.); R$_f$: 0.24 (ethyl acetate/n-hexane=1:3); IR (KBr) $v_{max}$: 3231, 2897, 1598, 1510, 1470, 1376, 1252, 1158, 1119, 826 cm$^{-1}$; $^1$H-NMR (400 MHz, DMSO-d$_6$): δ 2.80 (m, 2H, H-3 and H-4a), 3.01 (m, 1H, H-4b), 3.89 (t, J=10.4 Hz, 1H, H-2a), 4.14 (d, J=10.4 Hz, 1H, H-2b), 6.20 (d, J=2.4 Hz, 1H, H-8), 6.29 (dd, J=8.4, 2.4 Hz, 1H, H-6), 6.72 (d, J=8.4 Hz 2H, H-3', H-5'), 6.86 (d, J=8.4 Hz, 1H, H-5), 7.10 (d, J=8.4 Hz, 2H, H-2', H-6'), 9.18 (s, 1H, OH), 9.29 (s, 1H, OH); $^{13}$C-NMR (100 MHz, DMSO-d$_6$): δ 31.3, 37.2, 70.3, 102.5, 108.0, 112.6, 115.3, 128.3, 130.1, 131.7, 154.5, 156.2, 156.5; EIMS (70 eV) m/z (relative intensity, %): 242 (M$^+$, 58), 135 (25), 134 (40), 123 (88), 120 (100), 107 (39), 91 (37). Anal. calcd for $C_{15}H_{14}O_3$: C, 74.36; H, 5.82. found: C, 74.13; H, 5.90.

Ex. 5

Synthesis of 7-benzyloxy-hydroxy-3-(4-methoxyphenyl)-1-benzopyran (Compound 4)

Borane-dimethylsulfide complex (BH$_3$—SMe$_2$) (10 M, 1.14 mL, 11.4 mmol) in THF was added dropwise at 0° C. to a solution of compound 1 (1 g, 2.9 mmol) in THF (12 mL), and the resultant mixture was stirred at 0° C. for 4 hrs. After completion of the reaction, the mixture was quenched with H$_2$O (7 mL), and then continually stirred for 5 min, followed by addition of 10% NaOH (2 mL) and 37% H$_2$O$_2$ (0.36 mL). After stirring for 30 min, the mixture was extracted with $CH_2Cl_2$ (30 mL×5). The organic layers were combined and dried with anhydrous MgSO$_4$. After filtration, the filtrate was concentrated in vacuo, followed by purification via silica gel column chromatography (ethyl acetate/n-hexane=1:4), thus giving the title compound 4 as a colorless crystal (0.63 g, 60% yield).

Detected Properties of the Title Compound:

M.p.: 138-139° C. (lit: 140-142° C.); R$_f$: 0.26 (ethyl acetate/n-hexane=1:4); IR (KBr) $v_{max}$: 3370, 2921, 1617, 1509, 1459, 1250, 1174, 1033, 739 cm$^{-1}$; $^1$H-NMR (400 MHz, CDCl$_3$): δ 1.91 (d, J=5.2 Hz, 1H, OH), 3.10 (ddd, $J_{trans-cis}$=8.4, 6.8, 3.6 Hz, 1H, H-3), 4.23 (dd, $J_{gem-trans}$=11.2, 8.4 Hz, 1H, H-2a), 4.35 (dd, $J_{gem-cis}$=11.2, 3.6 Hz, 1H, H-2b), 4.87 (dd, J=6.8, 5.2 Hz, 1H, H-4), 5.04 (s, 2H, OCH$_2$Ar), 6.49 (d, J=2.4 Hz, 1H, H-8), 6.63 (dd, J=8.4, 2.4 Hz, 1H, H-6), 6.88 (d, J=8.8 Hz, 2H, H-3', H-5'), 7.16 (d, J=8.8 Hz, 2H, H-2', H-6'), 7.36 (d, J=8.4 Hz, 1H, H-5), 7.31-7.45 (m, 5H, ArH); $^{13}$C-NMR (100 MHz, CDCl$_3$): δ 46.2, 55.3, 68.2, 69.2, 70.0, 102.1, 108.7, 114.3, 117.3, 127.5, 128.0, 128.6, 128.9, 129.2, 130.6, 136.8, 155.2, 158.9, 159.7; EIMS (70 eV) m/z (relative intensity, %): 362 (M$^+$, 25), 344 (14), 253 (21), 214 (28), 213 (67), 150 (15), 135 (23), 92 (70), 91 (100). HRMS calcd for $C_{23}H_{22}O_4Na$ (M$^+$+Na): 385.1416; found: 385.1418. Anal. calcd for $C_{23}H_{22}O_4$: C, 76.22; H, 6.12. found: C, 75.85; H, 6.25.

Ex. 6

Synthesis of 7-benzyloxy-3-(4-methoxyphenyl)-1-benzopyran-4-one (Compound 5)

A solution of compound 4 as obtained in the above Example 5 (0.6 g, 1.66 mmol) in 1,4-dioxane (16 mL) was added with 2,3-dichloro-5,6-dicyanobenzoquinone (0.83 g, 3.66 mmol), and the resultant mixture was stirred and heated under reflux for 8 hrs. Thereafter, the mixture was quenched with saturated saline solution (50 mL) and extracted with $CH_2Cl_2$ (30 mL×5). The organic layers were combined and dried over anhydrous MgSO$_4$. After filtration, the filtrate was concentrated in vacuo, followed by purification via silica gel column chromatography (ethyl acetate/n-hexane=1:5), thus giving the title compound 5 as a colorless crystal (0.46 g, 78% yield).

Detected Properties of the Title Compound:

M.p.: 181-183° C. (lit: 180-182° C.); R$_f$: 0.54 (ethyl acetate/n-hexane=1:3); IR (KBr) $v_{max}$: 2953, 1628, 1603, 1511, 1444, 1248, 1208, 828 cm$^{-1}$; $^1$H-NMR (400 MHz, CDCl$_3$): δ 3.84 (s, 3H, OCH$_3$), 5.16 (s, 2H, OCH$_2$Ar), 6.92 (d, J=2.4 Hz, 1H, H-8), 6.97 (d, J=8.8 Hz, 2H, H-3', H-5'), 7.07 (dd, J=8.8, 2.4 Hz, 1H, H-6), 7.41 (m, 5H, ArH), 7.49 (d, J=8.8 Hz, 2H, H-2', H-6'), 7.90 (s, 1H. H-2), 8.22 (d, J=8.8 Hz, 1H, H-5); $^{13}$C-NMR (100 MHz, CDCl$_3$): δ 55.3, 70.5, 101.2, 113.9, 115.0, 118.6, 124.2, 124.8, 127.5, 127.8, 128.4, 128.7, 130.1, 135.7, 152.0, 157.8, 159.5, 162.9, 175.8; EIMS (70 eV) m/z (relative intensity, %): 359 ([M+1]$^+$, 7), 358 (M$^+$, 30), 207 (7), 92 (20), 91 (100), calcd for $C_{23}H_{18}O_4Na$: 381.1103; found; 381.1102. Anal. calcd for $C_{23}H_{18}O_4$: C, 77.08; H, 5.06. found: C, 76.79; H, 5.09.

Ex. 7

Synthesis of 7-hydroxy-3-(4-hydroxyphenyl)-1-benzopyran-4-one (daidzein, Compound 6a)

Under the protection of dry argon, a stirred solution of EtSH (20 mL) in $CH_2Cl_2$ (20 mL) was treated with AlCl$_3$ (2 g, 15 mmol) at 0° C. After stirring for 5 min, the mixture was added with compound 5 as obtained in the above Example 6 (0.2 g, 0.56 mmol). After stirring at 0° C. for 30 min, the mixture was quenched with water (50 mL), and then warmed up to 40° C. to remove $CH_2Cl_2$ and EtSH. Thereafter, the mixture was extracted with EtOAc (10 mL×6). The organic layers were combined, washed with a saturated NaCl solution (10 m×2), and dried with anhydrous MgSO$_4$. After filtration, the filtrate was concentrated in vacuo, followed by purification via silica gel column chromatography (ethyl acetate/n-hexane=1:6), thus giving the title compound 6a as a colorless crystal (0.13 g, 92% yield).

Detected Properties of the Title Compound:

M.p.: 329-330° C. (lit: 315-330° C.); $R_f$: 0.27 (ethyl acetate/n-hexane=1:1); IR (KBr) $v_{max}$: 3221, 1631, 1595, 1518, 1460, 1279, 1239, 1192, 843 cm$^{-1}$; $^1$H-NMR (400 MHz, DMSO-d$_6$): δ 6.80 (d, J=8.8 Hz, 2H, H-3', H-5'), 6.86 (d, J=2.0 Hz, 1H, H-8), 6.93 (dd, J=8.8, 2.0 Hz, 1H, H-6), 7.38 (d, J=8.8 Hz, 2H, H-2', H-6'), 7.96 (d, J=8.8 Hz, 1H, H-5), 8.28 (s, 1H, H-2), 9.54 (br s, 1H, OH), 10.79 (br s, 1H, OH); $^{13}$C-NMR (100 MHz, DMSO-d$_6$): δ 102.1, 114.9, 115.1, 116.6, 122.5, 123.5, 127.3, 130.1, 152.8, 157.2, 157.4, 162.5, 174.7; EIMS (70 eV) m/z (relative intensity, %): 254 (M$^+$, 93), 253 (56), 137 (100), 118 (74), 89 (48), 63 (46). Anal calcd for $C_{15}H_{10}O_4$: C, 70.86; H, 3.96. found: C, 70.62; H, 4.04.

Ex. 8

Synthesis of 7-hydroxy-3-(4-methoxyphenyl)-1-benzopyran-4-one (formononetin, Compound 6b)

Cyclohexene (0.5 mL) and Pd(OH)$_2$/C (0.05 g) was added to a stirred solution of compound 5 as obtained in the above Example 6 (0.2 g, 0.56 mmol) in ethanol (12 mL). The reaction mixture was stirred under a reflux temperature of 78° C. for 1 hr, and then cooled to room temperature. After filtration, the filtrate was concentrated in vacuo, followed by purification via silica gel column chromatography (ethyl acetate/n-hexane=1:2), thus giving the title compound 6b as a colorless crystal (0.14 g, 94% yield).

Detected Properties of the Title Compound:

M.p.: 263-264° C. (lit: 261-263° C.); $R_f$: 0.24 (ethyl acetate/n-hexane=1:2); IR (KBr) $v_{max}$: 3128, 2981, 1637, 1598, 1512, 1453, 1273, 1248, 1177, 1025, 808 cm$^{-1}$; $^1$H-NMR (400 MHz, DMSO-d$_6$): δ 3.78 (s, 3H, OCH$_3$), 6.87 (d, J=2.0 Hz, 1H, H-8), 6.94 (dd, J=8.4, 2.0 Hz, 1H, H-6), 6.98 (d, J=8.8 Hz, 2H, H-3', H-5'), 7.50 (d, J=8.8 Hz, 2H, H-2', H-6'), 7.97 (d, J=8.4 Hz, 1H, H-5), 8.33 (s, 1H, H-2), 10.81 (br s, 1H, OH); $^{13}$C-NMR (100 MHz, DMSO-d$_6$): δ 55.1, 102.1, 113.6, 115.2, 116.6, 123.1, 124.2, 127.3, 130.1, 153.1, 157.4, 158.9, 162.6, 174.6; EIMS (70 eV) m/z (relative intensity, %): 268 (M$^+$, 98), 267 (51), 132 (100), 89 (65), 63 (38). Anal calcd for $C_{16}H_{12}O_4$: C, 71.64; H, 4.51. found: C, 71.31; H, 4.52.

All patents and literature references cited in the present specification as well as the references described therein, are hereby incorporated by reference in their entirety. In case of conflict, the present description, including definitions, will prevail.

While the invention has been described in connection with specific embodiments thereof, it will be understood that it is capable of further modifications and this application is intended to cover any variations, uses, or adaptations of the invention following, in general, the principles of the invention and including such departures from the present customary practice within the art to which the invention pertains and as may be applied to the essential features hereinbefore set forth, and as follows in the scope of the appended claims.

We claim:

1. A process for preparing an isoflavonoid, comprising subjecting a compound of formula (I):

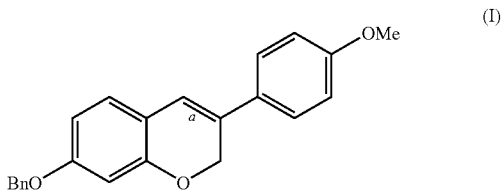

wherein:
a is a pi-bond;
Bn represents benzyl; and
Me represents methyl;
to at least a chemical reaction so that Bn in formula (I) is released.

2. The process of claim 1, wherein the isoflavonoid is equol, and the process comprises subjecting the compound of formula (I) to a chemical reaction so that in formula (I), a is converted to a single bond and Bn is released, followed by reaction with a demethylating reagent.

3. The process of claim 2, wherein the chemical reaction is conducted in the presence of a catalyst selected from the group consisting of palladium hydroxide on carbon and palladium on carbon.

4. The process of claim 3, wherein the chemical reaction is conducted in the presence of a hydrogen donor selected from the group consisting of: cyclohexene, cyclohexadiene, hydrogen gas, ammonium formate, and formic acid.

5. The process of claim 2, wherein the demethylating reagent is selected from the group consisting of: a combination of BCl$_3$ and n-tetrabutylammonium iodide; a combination of BCl$_3$ and ethanethiol; a combination of AlCl$_3$ and ethanethiol; a combination of AlCl$_3$ and n-tetrabutylammonium iodide; lithium chloride; and sodium ethylthiolate.

6. The process of claim 1, wherein the isoflavonoid is a compound of formula (II):

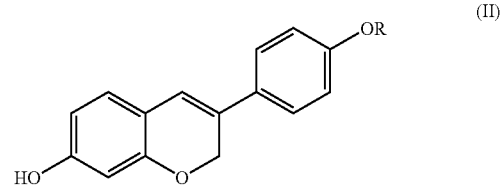

wherein R represents hydrogen or methyl,
and the process comprises subjecting the compound of formula (I) to a chemical reaction using a reagent capable of releasing at least Bn from formula (I).

7. The process of claim 6, wherein the reagent used in the chemical reaction is selected from the group consisting of: BCl$_3$; a combination of BCl$_3$ and n-tetrabutylammonium iodide; a combination of BCl$_3$ and ethanethiol; AlCl$_3$; a combination of AlCl$_3$ and ethanethiol; a combination of AlCl$_3$ and n-tetrabutylammonium iodide; lithium chloride; and sodium ethylthiolate.

8. A process for preparing an isoflavonoid of formula (III):

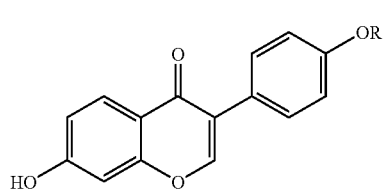

wherein R represents hydrogen or methyl, the process comprising:

(i) subjecting a compound of formula (I):

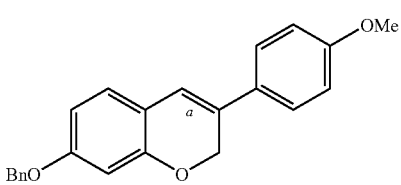

wherein a is a pi-bond, Bn represents benzyl, and Me represents methyl;

to a hydroboration reaction, followed by an oxidation reaction in the presence of a base, so as to form a compound of formula (IV):

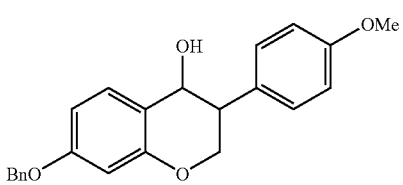

(ii) converting the compound of formula (IV) to a compound of formula (V):

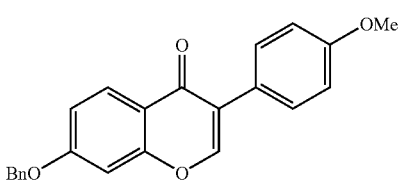

by an oxidation-dehydrogenation reaction using 2,3-dichloro-5,6-dicyanobenzoquinone; and (iii) subjecting the compound of formula (V) to a deprotection reaction such that at least Bn in formula (V) is released.

9. The process of claim 8, wherein the hydroboration reaction is conducted using a hydroborating reagent selected from the group consisting of borane-dimethylsulfide complex and $B_2H_6$.

10. The process of claim 8, wherein the oxidation reaction is conducted using an oxidizing reagent selected from the group consisting of $H_2O_2$ and $NaBO_3 \cdot 4H_2O$.

11. The process of claim 8, wherein the base is selected from the group consisting of NaOH and KOH.

12. The process of claim 8, wherein the deprotection reaction is conducted in the presence of a reagent that is capable of releasing at least Bn from formula (V) and is selected from the group consisting of $BCl_3$; a combination of $BCl_3$ and n-tetrabutylammonium iodide; a combination of $BCl_3$ and ethanethiol; $AlCl_3$; a combination of $AlCl_3$ and ethanethiol; a combination of $AlCl_3$ and n-tetrabutylammonium iodide; lithium chloride; and sodium ethylthiolate.

13. The process of claim 8, wherein the deprotection reaction is conducted in the presence of a catalyst selected from the group consisting of palladium hydroxide on carbon and palladium on carbon.

14. The process of claim 13, wherein the deprotection reaction is conducted in the presence of a hydrogen donor selected from the group consisting of: cyclohexene, cyclohexadiene, hydrogen gas, ammonium formate, and formic acid.

\* \* \* \* \*